United States Patent [19]

Ryan

[11] Patent Number: 5,448,967
[45] Date of Patent: Sep. 12, 1995

[54] PRODUCT FOR DEODORIZING AND SANITIZING HORSE STALLS, AND TO A PROCESS OF MAKING THE PRODUCT

[76] Inventor: Bernard E. Ryan, 3110 19th Ave., Forest Grove, Oreg. 97116

[21] Appl. No.: 189,908

[22] Filed: Feb. 1, 1994

[51] Int. Cl.$^6$ .............................................. A61L 11/00
[52] U.S. Cl. .................................. 119/171; 424/76.6; 422/5
[58] Field of Search .............. 119/171, 174, 161; 424/76.1, 76.21, 76.3, 76.6, 76.5; 422/5

[56] References Cited

U.S. PATENT DOCUMENTS 1,791,918  2/1931  Yamaji.
5,039,481  8/1991  Pacifici et al. .................... 424/76.6

FOREIGN PATENT DOCUMENTS 179063   10/1984  Japan ................................. 424/76.21
1143066  6/1986   Japan ................................. 424/76.21
2032958  2/1987   Japan ................................. 424/76.21
3084618  1/1988   Japan ................................. 424/76.2

Primary Examiner—John G. Weiss
Attorney, Agent, or Firm—Eugene M. Eckelman

[57] ABSTRACT

A grain cereal having a high level enzyme content is mixed with a bran having a high level incubating enzyme content to produce, when mixed with the grain cereal, synergistic, non-pathogenic enzymes that are capable of causing vigorous breeding of enzymes that starve out harmful bacteria in horse manure and urine and also accelerates decomposition of albumin to suppress and eliminate unpleasant odor. Also in the product and process, kelp is added for increasing the vigorous breeding of the enzyme and also a finely reduced germinated cereal of high level enzyme content is added to further increase the breeding of the enzymes. The product and process include a powdered ingredient of diatomaceous earth which serves as an insecticide, a desiccant, and extends the shelf life of the product.

10 Claims, No Drawings

PRODUCT FOR DEODORIZING AND SANITIZING HORSE STALLS, AND TO A PROCESS OF MAKING THE PRODUCT

BACKGROUND OF THE INVENTION

This invention relates to a product for deodorizing and sanitizing horse stalls, and to a process of making the product.

It is known that horse waste, namely, manure and urine, vary according to the food that the horses have eaten. Such waste consists principally of protein, for example, albumin, globulin, nuclein, pepton, mucin and their decomposition products, as well as carbohydrates, such as starch, cellulose, sugars and organic acids. When this substance decomposes, it usually produces organisms and gases of disagreeable odor such as indol, scatol, and other sulphites. Decomposing horse waste also contains conditions satisfactory for the breeding of harmful bacteria and insects.

The act or process of decomposing of the waste substances of horses is believed to be the result of the organisms of the simplest form, schizomycetes, bacteria, microbes, etc. Putrefaction only takes place when conditions are favorable for the life and growth of these organisms, for example, a temperature of from approximately 60°-80° F., a moderate humidity and limited access to air.

Solutions to problems in the general area of putrefaction of material and to eliminating odors as a result thereof have heretofore been used or sought. For example, it is well known to use lime for deodorizing horse stalls. Lime, however, immediately turns to slack lime and thus is short lived. U.S. Pat. No. 1,791,918 is concerned with a process of making a powdered product that deodorizes organic fertilizers, such as the excrement of livestock, fish, etc. and also accelerates ripening of such fertilizer and prevents the growth of harmful bacteria or organisms. The process of this patent consists in mixing dried and powdered cereal containing a large quantity of enzymes such as rice bran, barley bran, or wheat bran with water and fermented and then powdered. This powder is mixed with tricalcium phosphate and powder of barley, wheat, bean, etc. which contain a large quantity of enzymes. It is stated that these enzymes supply sufficient nutrition to yeasts and bacteria so as to make their breeding vigorous and thus drive out harmful bacteria. The process also is stated to accelerate the decomposition of albumin and convert it to an intermediate product free of odors.

SUMMARY OF THE INVENTION

It is an object of the present invention to provide a product that has substantial long lasting or infinite improvements over prior products and also a product that is particularly applicable for the treatment of horse stalls for the purpose of improved destruction of harmful organisms in both of the manure and urine, for deodorizing the manure and urine during its putrefaction and, for destroying insects, and to a process of making the product.

A more specific object of the invention is to provide a product and process that utilize a particular long lasting or infinite formulation of enzymes, kelp and diatomaceous earth for accomplishing the said improved purposes.

In carrying out these objects, the product comprises a grain cereal of the type having a high level enzyme content in combination with a bran also having a high level incubating enzyme content capable of producing, along with the grain cereal, synergistic, non-pathogenic enzymes that are capable of causing vigorous breeding of enzymes that starve out harmful bacteria in the horse manure and urine and also that accelerate putrefaction of albumin to suppress and eliminate the bad odor. The product also includes kelp for increasing the vigorous breeding of the enzymes. Furthermore, the product includes diatomaceous earth which serves as an insecticide and a desiccant. Furthermore, the product may include a finely reduced germinated grain of high level enzyme content which further increases the vigorous breeding of enzymes.

DETAILED DESCRIPTION OF A PREFERRED EMBODIMENT

The product of the invention comprises dried and reduced, such as powdered or granulated, grain cereals of the type that preferably contain a large quantity of hydrolytic and proteolitic enzymes for example, barley, wheat, rice or bean cereal in combination with a rice, barley, or wheat bran of specific enzyme content (A.ORYCAE AMYLASE) for incubution. Ground or liquid thorn kelp (ASCOPHILUM NODOSOM) is added to the mixture. After thorough mixing of the cereal and bran ingredients, and kelp, water is added and said mixture is fermented in a covered container at an effective fermentation temperature and time to provide complete or substantially complete fermentation. Temperature and time of fermentation depend on the type of substrate used. After the mixture has fermented, it is vacuum dried and reduced into a fine powder. This resulting dried powder is mixed with a dried powder of a germinated cereal that contains a large quantity of enzyme, for example, barley, wheat or bean bran. In a final step, dry ground diatomaceous earth is mixed thoroughly into this dry mixture.

As an example of proportions and process used in formulating the product the following is an example:

EXAMPLE 1

5 pounds of dried and powdered grain cereal, such as rice cereal, that contains a large quantity of hydrolytic and proteolitic enzyme was thoroughly mixed with 50 pounds of wheat bran or other bran with a high level incubation enzyme (A.ORYCAE AMYLASE) and 5 pounds of ground and powdered thorn kelp. This mixture was in turn mixed with 2½ gallons of water and then placed in a covered container and fermented at a temperature of approximately 90°. The water used was certified (sodium and chlorine free—American Public Health Assn. Standards and EPA) artesian well water at pH 7.1 which specifically does not kill the working bacteria or slow the breeding thereof. The fermentation period at this temperature was approximately two days. This fermentation time will vary according to the temperature used and the substrate that is used in the compound. After the fermentation period, the mixture is vacuum dried and then reduced to a fine powder or granules. This reduced mixture is thoroughly mixed with 5 pounds of dried and reduced, germinated grain containing a large quantity of enzyme, for example, barley, wheat or rice. Also added to the mixture at this time is approximately 1½ ounces of diatomaceous earth.

The above example illustrates the ingredients of a typical batch for making the present product and typical steps in a preferred process of making it. The proportions of ingredients as set forth is important but it is to be understood that the batch size may vary. The order of steps in the process may vary slightly. For example, the initial ingredients set forth in the example up to the fermentation step may be mixed in any order. Also, the final ingredients of cereal and diatomaceous earth can be mixed with the ground fermented product in reverse order.

According to the invention, there is provided a long lasting antibiotic substance derived from certain organisms that tend to destroy harmful organisms and acts as an antiseptic in destroying microorganisms that cause disease and fetid odors in horse waste such as in stalls and in other areas. The formulation and one of its functions is effective due to the cross linking and pre-fermentation of the grain cereals, kelp and bran. More particularly, the mixture of the high level enzyme cereal with the high level enzyme incubating bran produces the essential synergistic, non-pathogenic enzymes that cause vigorous breeding of enzymes that serve to starve out harmful bacteria that may create unpleasant odors. Also, it accelerates the decomposition of albumin and converts it into an intermediate product free from unpleasant odors. Further, the mixture in combination with kelp also fixes the ammonia produced by the organic acid and the superphosphate produced by the high level of enzymes also to suppress and to destroy unpleasant odor. The mixture also includes diatomaceous earth which is non-toxic to animals and humans but is both destructive and repellant to insects, thus serving as an insecticide. The diatomaceous earth also acts as an inert carrier and desiccant to prevent caking of the completed powder product for effective handling and storage. Diatomaceous earth also extends the shelf life.

It is to be understood that the form of my invention herein shown and described is to be taken as a preferred example of the same and that various changes in the shape, size and arrangement of parts may be resorted to without departing from the: spirit of my invention, or the scope of the subjoined claims.

Having thus described my invention, I claim:

1. A product for deodorizing and sanitizing horse stalls and for accelerating decomposition of horse manure and urine comprising a combination of a grain cereal of the type having a high level enzyme content, a bran of the type having a high level incubating enzyme content that produces, when mixed with said grain cereal synergistic, non-pathogenic enzymes that are capable of causing vigorous breeding of enzymes that starve out harmful bacteria in decomposing horse manure and urine and also accelerates decomposition of albumin to suppress and eliminate unpleasant odor, kelp for increasing the vigorous breeding of the enzymes, and a finally reduced germinated cereal of high level enzyme content.

2. The product of claim 1 including in the combination a powdered diatomaceous earth serving as an insecticide and a desiccant.

3. The product of claim 1 wherein the batch proportions of ingredients in the product comprise 5 pounds of said grain cereal, 50 pounds of said bran, 5 pounds of kelp, and 2.5 gallons of water.

4. The product of claim 1 wherein the batch proparations of ingredients in the product comprise 5 pounds of said grain cereal, 50 pounds of said bran, 5 pounds of kelp, 2.5 gallons of water, 5 pounds of finally reduced germinated cereal of high level enzyme content, and 1½ ounces of diatomaceous earth.

5. The process of making a product for deodorising and sanitizing horse stalls comprising mixing a powder of grain cereal of the type having a high level enzyme content with a bran of the type having a high level incubating enzyme that produces, when mixed with said grain cereal, synergistic, non-pathogenic enzymes that are capable of causing vigorous breeding of enzymes that starve out harmful bacteria in decomposing horse manure and urine and also accelerates decomposition of albumin to suppress and eliminate unpleasant odor, adding powdered kelp to said cereal and bran mixture, adding water to said mixture for initiating fermentation, allowing a fermentation period for said mixture, drying the fermented mixture, and reducing the dried fermented mixture to a powder.

6. The process of claim 5 including admixing a finely reduced germinated cereal of high level enzyme content with said reduced dried fermented mixture.

7. The process of claim 5 including admixing a finely reduced germinated cereal of high level enzyme content and diatomaceous earth with said reduced dried fermented mixture.

8. The process of claim 6 wherein said ingredients are mixed in the proportions of 5 pounds of said grain cereal, 50 pounds of said bran, 5 pounds of kelp, and 2.5 gallons of water.

9. The process of claim 6 wherein said ingredients are mixed in the proportions of 5 pounds of said grain cereal, 50 pounds of said bran, 5 pounds of kelp, 2.5 gallons of water, 5 pounds of finely reduced germinated cereal of high level enzyme content and 1½ ounces of diatomaceous earth.

10. The process of claim 9 wherein said water comprises certified artesian type well water.

* * * * *